United States Patent
Li et al.

(10) Patent No.: US 6,248,780 B1
(45) Date of Patent: Jun. 19, 2001

(54) COMPOUNDS FOR THE TREATMENT OF ESTROGEN-DEPENDENT ILLNESSES AND METHODS FOR MAKING AND USING THE SAME

(75) Inventors: Pui-Kai Li, Library; Kyle W. Selcer, Export, both of PA (US)

(73) Assignee: Duquesne University of the Holy Ghost, Pittsburgh, PA (US)

( * ) Notice: Subject to any disclaimer, the term of this patent is extended or adjusted under 35 U.S.C. 154(b) by 0 days.

(21) Appl. No.: 09/164,889

(22) Filed: Oct. 1, 1998

(51) Int. Cl.$^7$ .................................................. A61K 31/255
(52) U.S. Cl. .............................. 514/510; 514/518; 558/48
(58) Field of Search ............................... 558/48; 514/510, 514/518

(56) References Cited

U.S. PATENT DOCUMENTS

| | | |
|---|---|---|
| 5,047,431 | 9/1991 | Schickaneder et al. . |
| 5,273,992 | 12/1993 | Lo et al. . |
| 5,556,847 | 9/1996 | Johnson et al. . |
| 5,567,831 | 10/1996 | Li . |
| 5,571,933 | 11/1996 | Li et al. . |
| 5,616,574 | 4/1997 | Reed et al. . |
| 5,763,492 | 6/1998 | Johnson et al. . |

*Primary Examiner*—Samuel Barts

(74) *Attorney, Agent, or Firm*—Diane R. Meyers; Eckert Seamans Cherin & Mellot, LLC

(57) ABSTRACT

Novel sulfatase inhibitor/estrogen receptor blocker compounds useful in the treatment of estrogen dependent illnesses are disclosed. The compounds generally comprise a sulfamate moiety and an aromatic, estrogen receptor blocker moiety. Methods for synthesizing these compounds and using them in the therapeutic and/or prophylactic treatment of an estrogen-dependent disease are also disclosed.

16 Claims, 3 Drawing Sheets

COMPOUNDS FOR THE TREATMENT OF ESTROGEN-DEPENDENT ILLNESSES AND METHODS FOR MAKING AND USING THE SAME

FIELD OF THE INVENTION

The present invention relates to compounds for treatment of estrogen-dependent illnesses and methods for making and using the same. The compounds generally function by inhibiting sulfatase and/or blocking estrogen receptors. Methods of using these compounds provide both therapeutic and prophylactic treatment for estrogen dependent illnesses.

BACKGROUND OF THE INVENTION

Breast cancer is the most common malignancy in the United States. Clinically, breast cancer is divided into two types as defined by the amount of estrogen receptor (ER) present: estrogen dependent (ER+) and estrogen independent (ER−). It is estimated that approximately 30–40% of all breast cancers are estrogen dependent, and in postmenopausal women, the percentage is even higher. The most common treatment for estrogen-dependent breast cancers are endocrine treatments using an antiestrogen, such as tamoxifen, which blocks estrogen receptors. Progestins are also used although their mechanism of action is unknown. Other methods for treating estrogen-dependent breast cancer is through inhibition of estrogen biosynthesis with aromatase inhibitors. Aminoglutethimide, a non-steroidal aromatase inhibitor, and testolactone, a weak steroid aromatase inhibitor, are examples of compounds that have been used. Another non-steroidal aromatase inhibitor, CGS 16949A, and a steroidal aromatase inhibitor, 4-hydroxy-androstenedione, are at various stages of clinical trials.

All of the treatments described above deal with stopping the estrogen action through blocking estrogen receptors or inhibiting estrogen production. In estrogen dependent breast cancer patients, the estrogen levels in breast cancer cells are 5–10 times higher than in plasma. In postmenopausal women, the major pathway of estrogen production is through peripheral aromatization of circulating androstenedione (A) to estrone (E1), an estrogen with moderate biological activity. Estrone can be converted to estradiol (E2), the most potent endogenous estrogen, by 17β-hydroxysteroid dehydrogenase. The mean plasma levels of E1 and E2 in postmenopausal women are 100–150 pM and 30–40 pM, respectively.

Breast cancer cells accumulate high amounts of estrogens, even though studies have shown that there is no active uptake of estrogens by breast tumors. One of the possibilities to explain the high levels of estrogen is in situ production of estrogens from precursor substrates in the breast cancer cells. Indeed, aromatase has been found in breast cancer cells and conversion of androstenedione to estrone has been demonstrated. Another pathway for the in situ formation of estrogen is through the conversation of estrone sulfate (E1S) to estrone by the enzyme estrone sulfatase (estrone sulfatase pathway) as shown in FIG. 1. Estrone sulfate is the most abundant circulating estrogen in women (1–2 nM), which may represent an important reservoir of active estrogens.

The plasma level of estrone sulfate in postmenopausal breast cancer patients is reported to be significantly higher than in normal subjects. In addition, the concentration of estrone sulfate in the breast cancer cells of postmenopausal breast cancer patients is significantly higher than in plasma. Furthermore, estrone sulfatase has been consistently found in human breast cancer cells. High concentrations of estrone sulfate in blood and in breast cancer cells may provide a high flux of free estrogen to mammary tumors. Vignon et al., *Endocrinology* 106:1079–1086 (1980), demonstrated that in the MCF-7 human breast cancer cell line, estrone sulfate entered the cells and was metabolized, yielding unconjugated estrone and estradiol which were finally bound to nuclear estrogen receptors and eventually induced proteins of 46,000 and 160,000 molecular weight. Wilking et al., *Eur.J. Cancer* 16:1339–1344 (1980), were able to demonstrate the conversion of [$^3$H] estrone sulfate to [$^3$H] estrone and [$^3$H] estradiol by homogenates of mammary carcinoma tissue in vitro in 23 breast cancer patients. Pasqualini et al., *J. Steroid Biochem.* 34:155–163 (1989), reported that a high percentage of [$^3$H] estrone sulfate was converted to estradiol in different hormone-dependent mammary cancer cell lines (MCF-7, R-27, T47D), but little or no conversion was found in the hormone-independent mammary cancer cell lines (MDA-MB-231, MDA-MB436). Santen et al., *J. Clin. Endocrinol. & Metab.* 59:29–33 (1984), and *Am. NY Acad. Sci.* 464:126–137 (1986), evaluated the estrogen production from breast tumors via the estrone sulfate to estrone (sulfatase) pathway and compared it with the androstenedione to estrone (aromatase) pathway. When comparing the sulfatase with aromatase activity in human tumors at physiological levels of substrates, the amount of estrone produced through sulfatase was 10 times higher than through the aromatase pathway (2.8 pmol estrone/g protein vs 0.27 pmol/g protein) in human breast tumors. Santen suggested that this sulfatase pathway was significant and perhaps the primary means of local estrogen production in breast tumor tissues. In addition, despite the fact that aromatase inhibitors can cause a near total inhibition (95–98%) of peripheral aromatization of androstenedione to estrone, plasma levels of estrone and estradiol are sustained at a level of 45–65 % and estrone sulfate at 40–50%, the control levels in patients receiving aromatase inhibitor treatments. This residual amount of estrone sulfate may be a potential source of estrogens through the sulfatase pathway.

Preliminary reports indicate the importance of the estrone sulfatase pathway in supplying estrogenic steroids to support breast cancer growth. Inhibitors of this pathway may be potential therapeutic agents for the treatment of estrogen-dependent breast cancer. Among all the estrone sulfatase inhibitors, estrone-3-O-sulfamate (EMATE) is the most potent sulfatase inhibitor ever reported. It is classified as an active-site directed irreversible inhibitor. Estrone may be released during the inactivation of sulfatase by EMATE, however, thereby making the inhibitor itself estrogenic. This compound is therefore not useful in the treatment of estrogen-dependent illnesses.

Reed and co-workers reported the sulfatase inhibitory activities of estrone-3-O-methylthiophosphonate, estrone-3-O alkyl and aryl sulfonates, estrone-3-O-phosphonates and thiophosphonates and estrone sulfonates in: Duncan et al., "Inhibition of estrone sulfatase activity by estrone-3-methylthiophosphonate", *Cancer Res.* 53:298–303 (1993);

Howarth et al., "Phosphonates and thiophosphonates as sulfate surrogates: Synthesis of estrone-3-methylthiophosphonate, a potent inhibitor of estrone sulfatase", Bioorg. Med. Chem. Lett. 3:313–318 (1993); Howarth et al., "Estrone sulfamates: Potent inhibitors of estrone sulfatase with therapeutic potential", J. Med. Chem. 37:219–221 (1994); and Purohit, et al., "In vivo inhibition of Oestrone Sulphatase and Dehydroepiandrosterone Sulphatase by Oestrone-3-O-sulphamate", Int. J. Cancer, 63:106–111 (1995).

Li and co-workers reported the synthesis and sulfatase inhibitory activities of sulfonate and its analogues, methylene sulfonates and phosphates that contain the estrone nucleus in Li et al., "Synthesis and biochemical studies of estrone sulfatase inhibitors", Steroids, 58:106–111 (1993); Dibbelt et al, "Inhibition of human placental sterylsulfatase by synthetic analogs of estrone sulfate", J. Steroid Biochem. Molec. Biol., 50 (516):261–266 (1994); and Li et al., "Estrone sulfate analogs as estrone sulfatase inhibitors", Steroids 60:299–306 (1995). Estrone-3-amino derivatives are reported in Selcer et al., "Inhibition of Placental Estrone Sulfatase Activity and MCF-7 Breast Cancer Cell Proliferation by Estrone-3-amino Derivatives", J. Steroid Biochem. Molec. Biol., 591:83–91 (1996).

U.S. Pat. No. 5,567,831 is directed to the use of non-steroidal sulfatase inhibitor compounds in the treatment of estrogen dependent illnesses.

U.S. Pat. No. 5,571,933 is directed to derivatives of estra 1,3,5(10)triene-17-one, 3-amino compounds and methods for using these compounds in the treatment of estrogen dependent illnesses.

U.S. Pat. Nos. 5,556,847 and 5,763,492 are directed to steroidal and non-steroidal sulfatase inhibitors, respectively, and methods for using these inhibitors to effect memory enhancement. Use of these inhibitors in the treatment of estrogen dependent illnesses is not disclosed.

U.S. Pat. No. 5,616,574 discloses steroid sulphatase inhibitors and methods of using the same. The compounds are potent estrogens and metabolize to form estrones, in contrast to the compounds of the present invention.

U.S. Pat. No. 5,047,431 discloses derivatives of 1,1,2-triphenylbut-1-ene, also known as tamoxifen. The U.S. Pat. No. 5,047,431 compounds have a hydroxy group attached at the 3' position of the phenyl ring on the C-atom 1 with respect to the position of the unsubstituted phenyl group on the C-atom 2 of the double bond.

U.S. Pat. No. 5,273,993 discloses compounds having at least one aminosulfonyloxy radical and the use of such compounds in the treatment of chronic arthritis or osteoporosis.

There remains a need for potent sulfatase inhibitors that are metabolically stable, more selective and devoid of estrogenic activity.

SUMMARY OF THE INVENTION

The present invention has met the above described needs by providing compounds useful as steroid sulfatase inhibitors. The present compounds offer a further benefit over the compounds reported in the art in that they also have ability to block estrogen receptors. These compounds have the general formula:

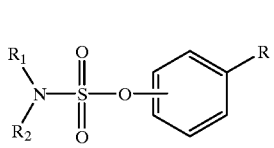

(1)

wherein the aromatic ring together with the R group represent a moiety that blocks an estrogen receptor; wherein $R_1$ and $R_2$ are independently selected from the group consisting of hydrogen and a lower alkyl group having between about one and six carbons; and wherein the sulfamate group is attached to the 2'C, the 3'C or the 4'C of the aromatic ring.

In addition, the present invention relates to methods for using the present compounds in the treatment of estrogen-dependent illnesses. These methods generally comprise incorporating one or more of the compounds into a suitable pharmaceutical carrier and administering a therapeutically or prophylactically effective amount of the compound to a patient.

It is an object of this invention to provide compounds for substantially inhibiting the steroid sulfatase enzyme produced in the body.

Another object of the invention is to provide compounds that block estrogen receptors.

It is a further object of the invention to provide compounds that function both as sulfatase inhibitors and estrogen receptor blockers.

It is a further object of the present invention to provide compounds having activity against estrogen dependent illnesses.

Yet another object of the invention is to provide methods for therapeutically or prophylactically treating a patient having an estrogen dependent illness.

It is another object of this invention to provide compounds for the treatment of estrogen-dependent illnesses that are not metabolized to compounds that are estrogenic.

These and other objects of the invention will be more fully understood to those skilled in the art upon review of the following description and appended claims.

DETAILED DESCRIPTION OF THE INVENTION

Figure 1:
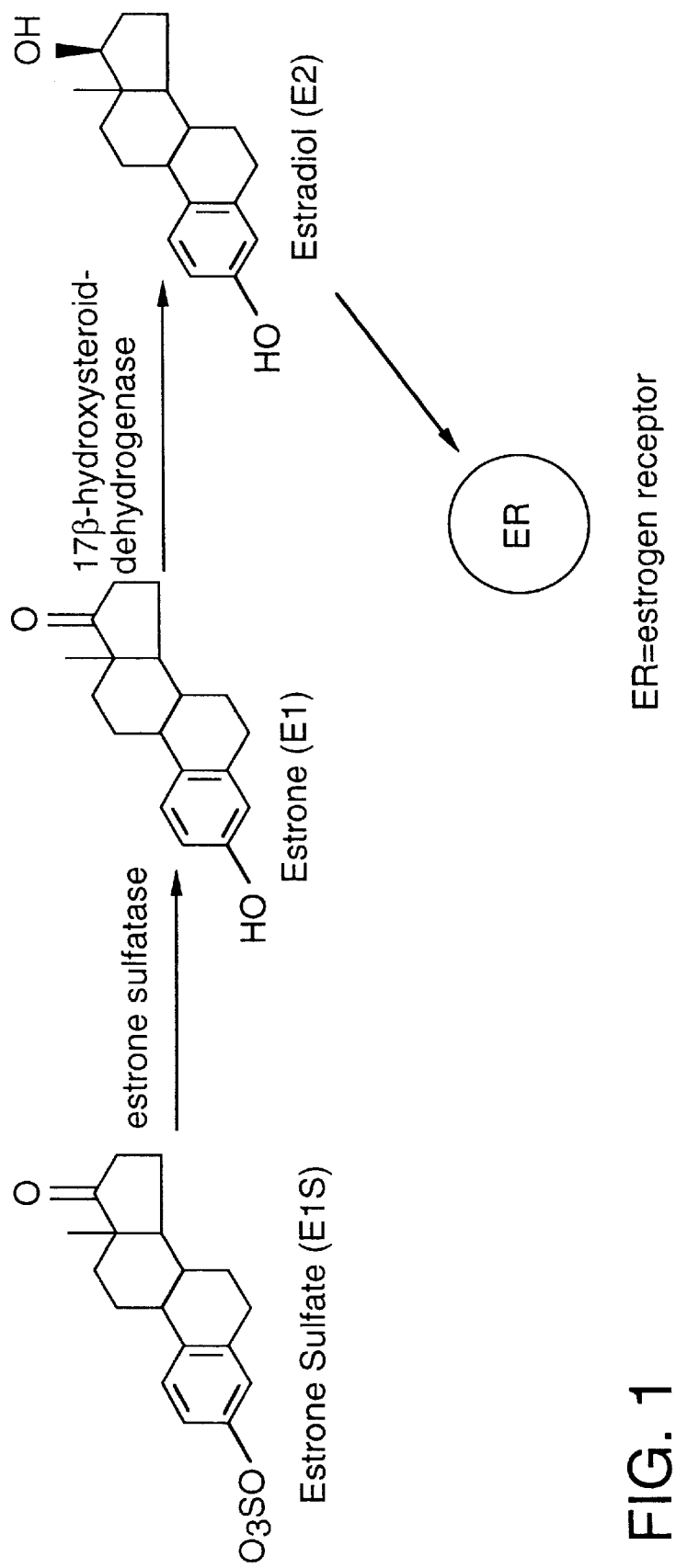
FIG. 1 generally illustrates the estrone sulfatase pathway.

As used herein, the term "patient" refers to members of the animal kingdom including but not limited to human beings.

The present invention relates to compounds having the formula (1):

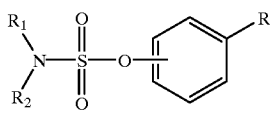
(1)

wherein the aromatic ring together with the R group represent a moiety that blocks an estrogen receptor; wherein $R_1$ and $R_2$ are independently selected from the group consisting of hydrogen and a lower alkyl group having one to six carbons; and wherein the sulfamate group is attached to the 2'C, the 3'C, or the 4'C of the aromatic ring.

A preferred embodiment of the above compound is represented by formula (2):

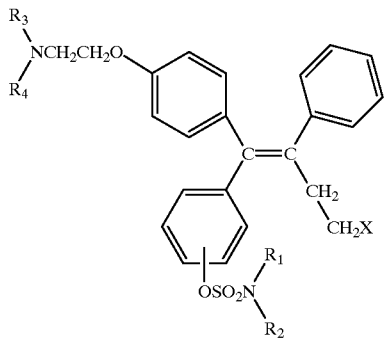
(2)

wherein $R_1$ and $R_2$ are independently selected from the group consisting of hydrogen 10 and a lower alkyl group having 1 to 6 carbons; wherein $R_3$ and $R_4$ are independently selected from the group consisting of hydrogen and a lower alkyl group having 1 to 6 carbons or $R_3$ and $R_4$ together comprise a cyclic structure having 4 to 6 carbons; wherein X is selected from the group consisting of hydrogen, a lower alkyl group having 1 to 4 carbons, OH, $NH_2$ and a halogen selected from fluorine, chlorine, bromine and iodine; and wherein the sulfamate group is attached at either the 2', 3'or 4' position of the aromatic ring.

A variation of formula 2, also a preferred embodiment of the compounds of the present invention, is represented by formula (3):

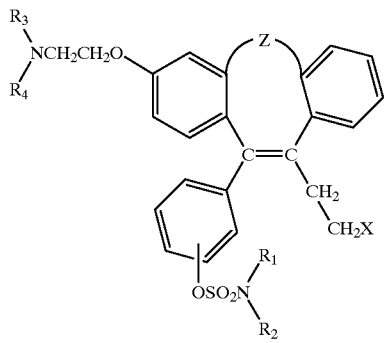
(3)

wherein $R_1$ through $R_4$ are as described above; X is as described above; Z is $(CH_2)_n$; and n equals 1 to 4.

In preferred embodiments of formulas 2 and 3, $R_3$ and $R_4$ equal $CH_3$, $R_1$ and $R_2$ equal H, X equals H or Cl and the sulfamate group is in the 4' position; for formula 3, n is preferably equal to 2.

As will be appreciated by those skilled in the art, the compounds of the present invention represented by formulas 2 and 3 are derivatives of (Z)4-hydroxytamoxifen ("tamoxifen"). In these formulas, therefore, the moiety represented by the aromatic ring together with the R group, as shown in formula 1, is tamoxifen or a tamoxifen derivative. As used herein, the term "tamoxifen derivative" refers to compounds having the basic triphenylethylene structure of the tamoxifen molecule, but having the variations such as those defined above as $R_1$ through $R_4$, X, and Z; other substituents and variations of the tamoxifen molecule are also within the scope of the present invention. Tamoxifen and its derivatives are known to block an estrogen receptor. The moiety represented by the aromatic ring to which is substituted an R group, as represented in formula 1, can be any compound that, like tamoxifen, functions to block estrogen receptors. Any estrogen receptor blocker having at least one aromatic ring to which can be attached a sulfamate group is therefore within the scope of the present invention. Examples include, but are not limited to, other triphenylethylene compounds. One skilled in the art could determine if a compound functions to block an estrogen receptor by utilizing the uterine weight gain assay described, for example, by Selcer and Li, *J. Steroid Biochem. Molec. Biol.*, Vol. 52, No. 3, pp. 281–286 (1995).

FIG. 1 depicts the production of estrogens through the estrone sulfatase pathway. As shown in that reaction scheme, estrone sulfate (E1S) is converted to estrone (E1) by the enzyme estrone sulfatase. Estrone is then converted to estradiol (E2) by the enzyme 17β-hydroxy steroid-dehydrogenase. The estradiol form of the compound is then able to bind with estrogen receptors stimulating tumor cell growth in estrogen-dependent forms of cancer.

Sulfamate compounds to which are attached a steroid ring system have been reported for the treatment of estrogen-dependent illnesses. The steroid ring system, or nucleus, is comprised of four rings, three of which are six membered (A, B and C) and one of which is five membered (D). As noted above, however, such compounds themselves break down to estrogen, thereby also contributing to the growth of the tumor cells. Such compounds function by inhibition of estrone sulfatase. It has been shown that the B, C and D rings of the steroid are not necessary for recognition of the sulfatase; all that is needed is the "A" ring of the steroid and the sulfamate moiety. The "A" ring will be understood by those skilled in the art as the aromatic ring in the steroid nucleus which is attached to the sulfamate moiety. The present compounds contain an aromatic ring attached to a sulfamate moiety. The sulfamate moiety recognizes and binds to the steroid sulfatase or estrone sulfatase, thereby preventing the conversion of estrone sulfate to estrone. Upon binding of the sulfate moiety with the enzyme, the aromatic ring portion of the present compounds, together with the R group, are believed to be released. The aromatic ring/R group moiety, which by definition is itself a compound that can block estrogen receptors, is then free to function in this manner. As noted above, blocking of estrogen receptors prevents estrogen from binding to the receptor, thereby preventing the estrogen from stimulating growth of cancer cells.

Although the inventors do not wish to be bound by any particular mechanism, it is believed that the compounds of the present invention have a two-fold effect in the treatment of estrogen-dependent illnesses: the sulfate moiety binds to and inhibits the steroid sulfatase activity; and an estrogen receptor blocker moiety binds to estrogen receptors thereby preventing estrogen molecules from attaching to estrogen receptors and promoting tumor cell growth. Thus, the effect of the compounds of the present invention is additive because the compound serves to inhibit estrogen production and stimulation of tumor cells in two ways.

Figure 2:
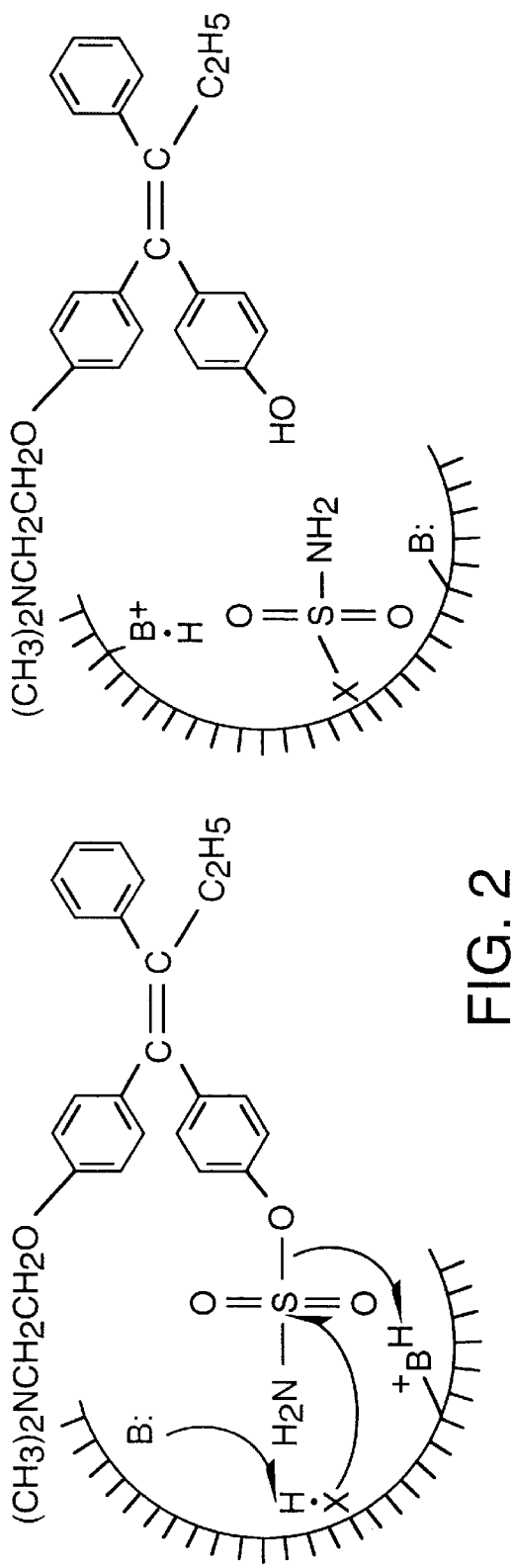
FIG. 2 illustrates the proposed mechanism of steroid sulfatase inactivation by (Z)-4-hydroxytamoxifen sulfamate.

A proposed mechanism of a preferred embodiment of the present invention is depicted in FIG. 2. There, the aromatic ring/R moiety is tamoxifen. The sulfamate portion of the compound becomes bound to and inhibits the steroid sulfatase. Upon binding to the sulfatase, it is believed that the tamoxifen moiety is then released and is thereby free to block estrogen receptors.

Figure 3:
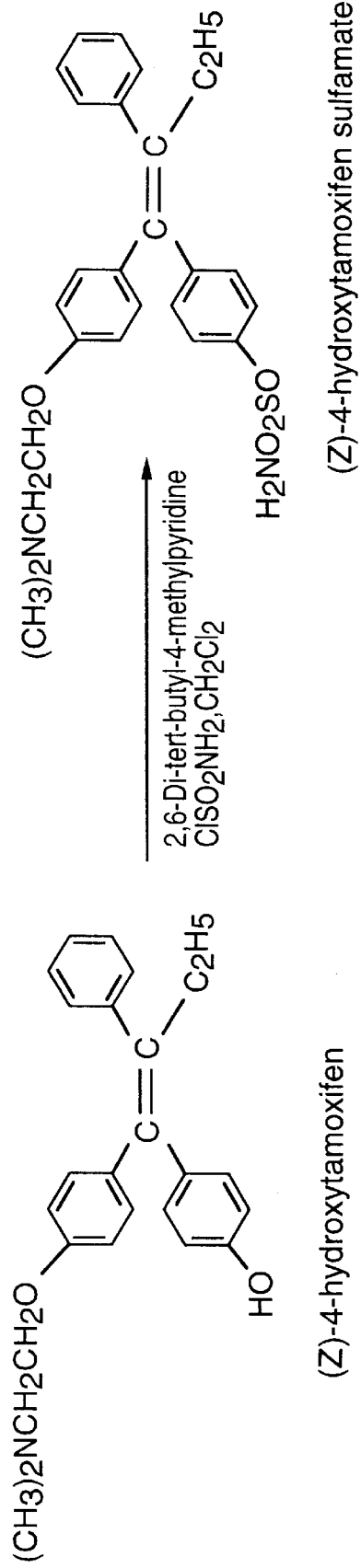
FIG. 3 illustrates the scheme for preparing compounds according to the methods of Example 1.

The present invention is further directed to the synthesis of the above-described compounds. This synthesis generally includes the addition of a sulfamate moiety to a nonsteroidal antiestrogen. The synthesis of a preferred compound is summarized in FIG. 3. FIG. 3 depicts use of (Z)4-hydroxytamoxifen as the starting material to which is added 2,6-Di-tert-butyl4-methylpyridine and sulfamoyl chloride. The result is a (Z)4-hydroxy tamoxifen sulfamate compound. It will be appreciated that the synthesis of the compound as depicted in FIG. 3 is representative of the synthesis of all of the compounds of the present invention. The particular tamoxifen sulfamate compound prepared in FIG. 3 is generally represented by formula 2 above, wherein $R_1$ and $R_2$ are both hydrogen, $R_3$ and $R_4$ are both $CH_3$ and X is also hydrogen. The methods of synthesizing the sulfamate compounds of the present invention follow this general reaction scheme, which is described in more detail in the example section.

The present invention is further directed to methods for using the compounds described above to therapeutically and/or prophylactically treat a patient for an estrogen dependent illness. Such illnesses include, but are not limited to, breast cancer, vaginal cancer, endometrial cancer, ovarian cancer and endometriosis.

The methods of the present invention include the steps of: a) incorporating one or more of the compounds of the present invention in a suitable pharmaceutical carrier; and b) administering either a therapeutically effective dosage or a prophylactically effective dosage of the compound or compounds incorporated in the carrier to a patient.

The term "suitable pharmaceutical carrier" refers to any carrier known in the pharmaceutical arts for administration of compounds to a patient. Any suitable pharmaceutical carrier can be used according to the present invention, so long as compatibility problems do not arise. A preferred pharmaceutical carrier is physiologic saline (0.9% sodium chloride), 95% dextrose in water.

Administration of an effective dosage to a patient can be accomplished by parenteral injection, such as intravenously, intrathecally, intramuscularly or intra-arterially. The compounds can also be administered orally or transdermally, or by any other means known to those skilled in the art. Oral administration is preferred.

As used herein, the term "therapeutically effective amount" refers to that amount of one or more of the compounds of the present invention required to therapeutically treat a patient. Such treatment is appropriate in patients having an estrogen-dependent illness. Similarly, the term "prophylactically effective amount" refers to that amount of one or more of the compounds of the present invention needed to prophylactically treat a patient. Such treatment is appropriate in patients who, for example, undergo surgery to remove cancerous growths; the compounds of the present invention would be administered to inhibit growth of any tumorous cells that were not removed by the surgery or to inhibit growth of any new tumor cells which appear.

As will be appreciated by those skilled in the art, the dosage of compound given, the route of administration and the duration of therapy will be dependent upon the individual being treated, taking into consideration such factors as the particular estrogen dependent illness being treated, the body weight of the patient, other therapies being employed to treat the patient, and the condition, clinical response and tolerance of the patient. Dosage, administration, and duration of therapy can be determined by one skilled in the art upon evaluation of these and other relevant factors. A typical patient will be a post-menopausal female or pre-menopausal female who has been ovariectomized. Although the dosage and administration will vary from patient to patient, a typical dose will range between 1 mg and 2 mg per kg of body weight, and will be administered daily.

The present invention provides numerous advantages over treatments known in the art. Because the compounds of the present invention are believed to have both steroid sulfatase inhibition activity and estrogen receptor blocking activity, there are two means by which these compounds prevent the growth of estrogen-dependent tumors in cancers. As a result, the use of the compounds of the present invention provides an additive effect not seen with other drugs. In addition, many of the drugs which block estrogen receptors, such as tamoxifen, are known to be nontoxic to the patient thereby minimizing the negative effects associated with other chemotherapeutic regimes. Finally, the compounds of the present invention are nonsteroidal; therefore the breakdown of these compounds does not contribute to the production of more estrogen. These and other advantages of the invention will be apparent to those skilled in the art.

EXAMPLES

The following examples are intended to illustrate the invention and should not be construed as limiting the invention in any way.

For all of the examples, chemicals and silica gel were purchased from Aldrich Chemical Company (Milwaukee, Wis.). The chemicals were checked for purity by thin layer chromatography and NMR. Biochemicals, estrone and estrone sulfate were obtained from Sigma Chemical Company (St. Louis, Mo.). [6,7-$^3$H]Estrone sulfate was purchased from Dupont Company. Melting points were determined on a Thomas Hoover capillary melting point apparatus and were uncorrected. Proton NMR spectra were obtained with a Bruker WH-300 (300 MHz) spectrophotometer. Elemental analyses were performed by Atlantic Microlab Inc. (Norcross, Ga.). Radioactive samples were analyzed with a Packard Tri-Carb 4530 Liquid Scintillation Counter. The liquid scintillation cocktail was Ecolume (ICN, Costa Mesa, Calif.).

Example 1
Synthesis of (Z)-4Hydroxytamoxifen Sulfamate

To a solution of (Z)-4-hydroxytamoxifen (150 mg, 0.39 mmol) and 2,6-di-tert-butyl4-methylpyridine (246 mg, 1.2 mmol) in $CH_2Cl_2$ (12 ml) was added sulfamoyl chloride (347 mg, 3 mmol) portionwise with stirring. After stirring for three hours, the solution was washed with water until neutral, dried over $Na_2SO_4$, and evaporated under reduced pressure to form yellowish residue. Purification of the residue by silica gel chromatography eluted with petroleum ether:ethyl acetate (4:1) gave the pure compound as a foam (168 mg, 93% yield). $^1$H NMR (300 MHz, DMSO-$d_6$) $\delta$0.85 (t, 3H, J=7.2 Hz, $CH_3$), 2.18 (s, 6H, $N(CH_3)_2$), 2.40 (q, 2H, J=7.2 Hz, $CH_2CH_3$), 2.54 (t, 2H, J=5.7 Hz, $CH_2N$), 3.90 (t, 2H, J=5.7 Hz, $CH_2O$), 6.61 (d, 2H, J=8.1 Hz, ArH), 6.75 (d, 2H, J=8.1 Hz ArH), 7.12 –7.30 (m, 9H, ArH), 8.04 (brs, 2H, NH2). Analysis calculated for $C_{26}H_{30}N_2O_4S \times 0.5\ CH_3COOC_2H_5$; C, 65.86; H, 6.75; N, 5.49; S, 6.28. Found C, 65.70; H, 6.51; N, 5.81; S, 6.28.

Example 2
Rat Liver Microsome Sulfatase Assay Procedure

The (Z)-4-Hydroxytamoxifen sulfamate prepared according to Example 1 was tested in vitro using rat liver microsome as a source of sulfatase.

Livers, obtained from juvenile female Sprague-Dawley rats, were minced with scissors in ice-cold 0.25M Tris-sucrose buffer (1:2 w:v) and homogenized with a Tissue Tearor using three 30 sec bursts. The nuclear fraction was pelleted by centrifugation at 1500 xg for 15 min at 4° C. The supernatant was decanted and centrifuged at 10,000 xg for 30 min at 4° C. to pellet the mitochondrial fraction. The resulting supernatant was removed and centrifuged at 100,000 xg to yield the microsomal fraction. The microsomal pellet was resuspended in 50 mM Tris-HCl buffer (1:5 w:v) and protein from the microsomal suspension was determined by using the BCA assay.

$^3$H-estrone sulfate (53 Ci/mmol) was diluted in 50 mM Tris-HCl buffer and 50 $\mu$l (140,000 dpm) of the solution were added to all assay tubes. Radioinert estrone sulfate was dissolved in ethanol and then diluted into 50 mM Tris-HCl buffer. To achieve final concentrations of estrone sulfate, 100 $\mu$l of desired concentrations were added to the assay tubes. Compounds prepared according to Example 1 were dissolved in ethanol and then diluted in 50 mM Tris-HCl buffer. To achieve a final concentration of 10 $\mu$M, 50 $\mu$l of each compound were added to designated assay tubes. Tubes not having the compounds of Example 1 contained 50 $\mu$l of an equal concentration of ethanol and 50 mM Tris-HCl buffer. Rat liver microsomes were diluted with Tris-HCl buffer to 25 $\mu$g/300 $\mu$l buffer. The assay was initiated by addition of microsomes (300 $\mu$l) in 15 sec intervals to the tubes containing the compounds. Control samples with no inhibitors received the addition of microsomes while control samples with no membranes did not. After 20 min of incubation at 37° C., 500 $\mu$l of 0.1 N NaOH were added to all tubes in 15 sec intervals to quench the assay. Extraction of radiolabeled estrone was accomplished by adding 3 ml of toluene to each tube. The quenched samples were vortexed for 1 min and centrifuged at 1,500 x g for 5 min. Two 500 $\mu$l aliquots of the organic phase were removed from each sample with the addition of four ml of scintillation cocktail. All aliquots were placed in the Packard Tri-Carb scintillation counter for determination of product formation. Each sample was run in duplicate. Product formation for samples containing an inhibitor was compared to that of the control samples, and data for Km and Ki were assessed through Michaelis Menten and Lineweaver-Burk calculations. Km is the dissociation constant of the enzyme-substrate complex. Ki is the dissociation constant of enzyme-inhibitor complex. Results are shown in FIG. 4.

Figure 4:
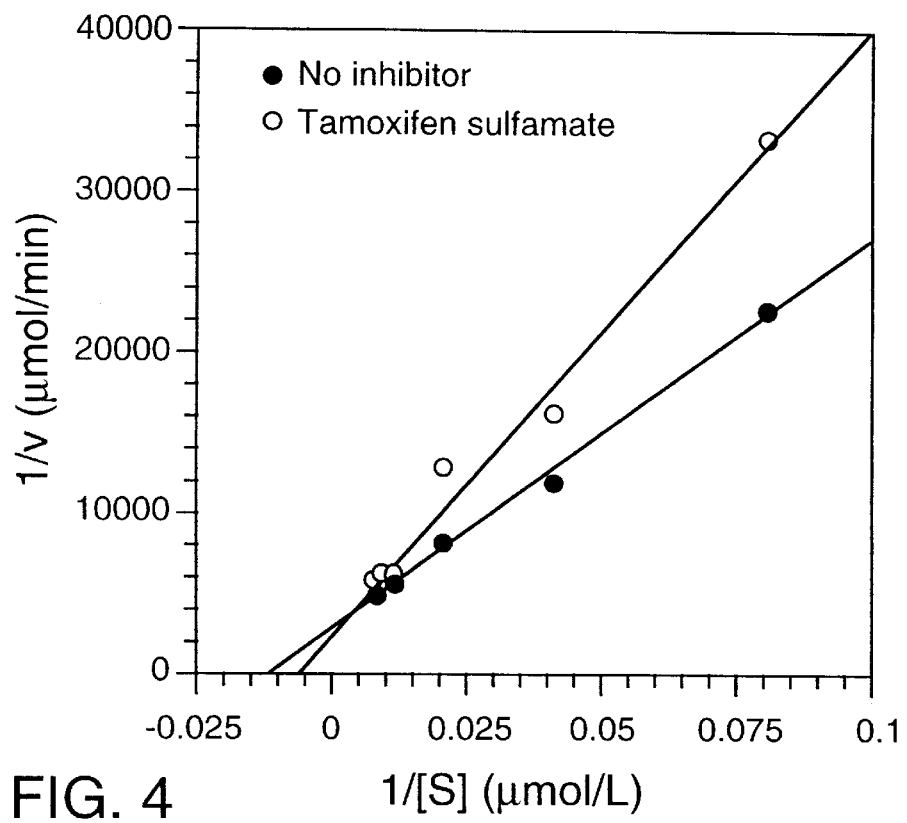
FIG. 4 is a double reciprocal plot demonstrating the inhibition of estrone sulfatase activity in rat liver microsomes by tamoxifen sulfamate, determined according to the methods of Example 2.

FIG. 4 is a double reciprocal plot (Lineweaver-Burk) demonstrating the inhibition of estrone sulfatase activity in rat liver microsomes by tamoxifen sulfamate. In FIG. 4, the rate of enzyme reaction is measured in the absence of inhibitor and in the presence of a fixed concentration of inhibitor, and the two sets of data are compared on the double reciprocal plot. It is shown that the maximum velocity of the enzyme reaction does not change and the Km is increased. This demonstrates that tamoxifen sulfamate is a competitive inhibitor. Based upon this plot it was determined that the Ki of tamoxifen sulfamate was approximately 17 $\mu$M.

Example 3
Intact Breast Cancer Cell Estrone Sulfatase Assay

The ability of the compound prepared according to Example 1 to block hydrolysis of estrone sulfate was examined using intact monolayers of MDA-MB-231 breast cancer cells.

Figure 5:
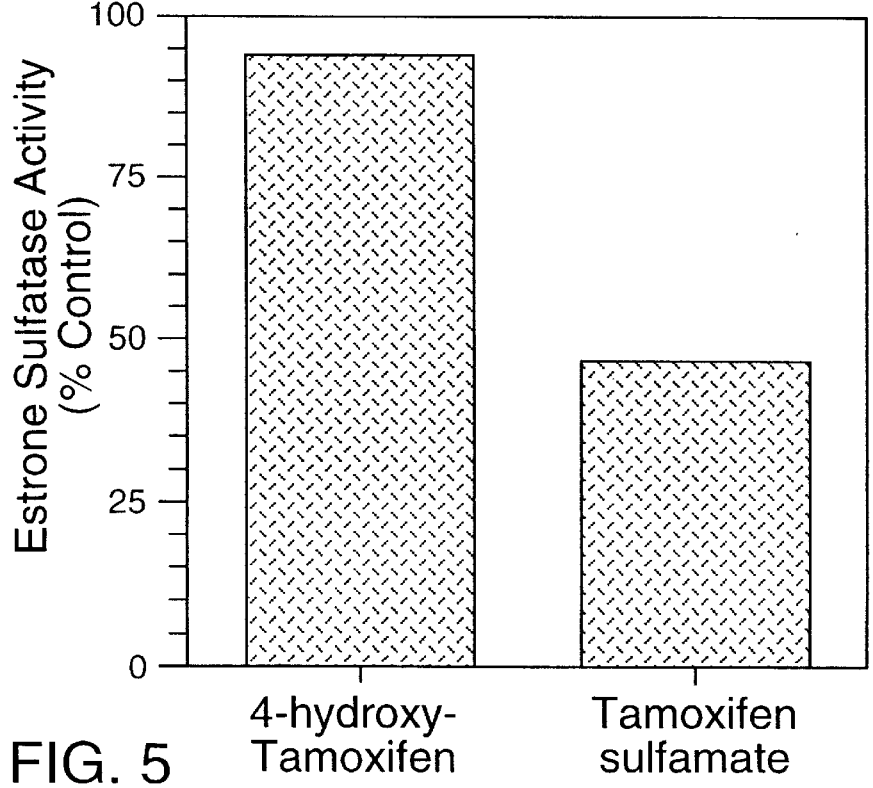
FIG. 5 is a graph comparing the inhibition of estrone sulfatase activity in human breast cancer cells by tamoxifen sulfamate and 4-hydroxytamoxifen, determined according to the methods of Example 3.

MDA-MB-231 cells were plated into 6-well dishes at approximately 1×10$^6$ cells/well in growth medium and incubated at 37° C. overnight to facilitate adherence to the plates. The growth medium contained 0.2% (v/v) sodium bicarbonate, 5% heat-inactivated fetal-calf serum, 10 mg/mL gentamicin, and 1% (v/v) antibiotic/antimycotic. Following incubation, growth medium was removed and replaced with growth medium containing $^3$H-estrone sulfate (100,000 dpm/ml), with or without the compound of Example 1 (10 $\mu$M). Cells were incubated for 18 h, then plates were cooled for 15 min. Medium from each well (500 $\mu$L) was aliquoted into 16–100 mm tubes. Three mls of toluene were added to each tube for extraction of unconjugated steroids. The tubes were vortexed for 1 min and then centrifuged at 2500 x g for 5 min to separate the aqueous and organic phases. One mL of the organic phase (containing radiolabeled unconjugated steroids) was transferred to scintillation vials and 5 ml scintillation cocktail was added. Total radioactivity was counted using a Packard Tri-carb scintillation counter at 50% efficiency for $^3$H. All extractions were performed in duplicate and all treatments were run in triplicate. Product formation for samples containing an inhibitor was compared to that of the control samples run simultaneously and is reported as percent inhibition of control samples. Results are shown in FIG. 5, which indicates that at 10 $\mu$M concentration, tamoxifen sulfamate can inhibit about 50% of the estrone sulfatase in the breast cancer cells MDA-MB-231. Data in FIG. 5 are presented as percentage of control, which is estrone sulfatase activity in the absence of inhibitors.

Whereas particular embodiments of this invention have been described above for purposes of illustration, it will be evident to those skilled in the art that numerous variations of the details of the present invention may be made without departing from the invention as defined in the appended claims.

What is claimed is:

1. A compound having the formula (1):

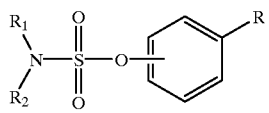
(1)

wherein the aromatic ring together with the R group represent a moiety that blocks an estrogen receptor;
wherein $R_1$ and $R_2$ are independently selected from the group hydrogen and a lower alkyl group having 1 to 6 carbons; and
wherein the sulfamate group is attached to the 2'C, 3'C or 4'C of the aromatic ring.

2. A compound having the formula (1):

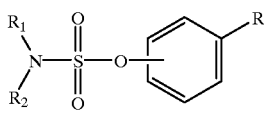
(1)

wherein the aromatic ring together with the R group represent a moiety that blocks an estrogen receptor;
wherein $R_1$ and $R_2$ are independently selected from the group hydrogen and a lower alkyl group having 1 to 6 carbons;
wherein the sulfamate group is attached to the 2'C, 3'C or 4'C of the aromatic ring; and
wherein the moiety represented by the aromatic ring together with the R group is selected from the group tamoxifen and tamoxifen derivatives.

3. The compound of formula (1) having the formula:

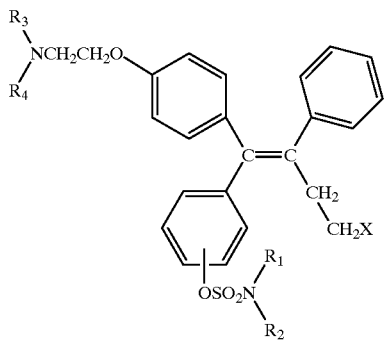
(2)

wherein $R_1$ and $R_2$ are independently selected from the group hydrogen and a lower alkyl group having 1 to 6 carbons;

wherein $R_3$ and $R_4$ are independently selected from the group hydrogen and a lower alkyl group having 1 to 6 carbons, or $R_3$ and $R_4$ together comprise a cyclic structure having 4 to 6 carbons;
wherein X is selected from the group hydrogen, a lower alkyl group having 1 to 4 carbons, OH, $NH_2$ and a halogen selected from fluorine, chlorine, bromine and iodine; and
wherein the sulfamate group is attached at either the 2', 3' or 4' position.

4. The compound of claim 2 having the formula (3):

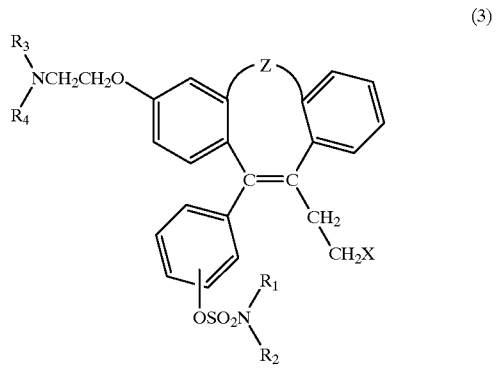
(3)

wherein $R_1$ and $R_2$ are independently selected from the group hydrogen and a lower alkyl group having 1 to 6 carbons;
wherein $R_3$ and $R_4$ are independently selected from the group hydrogen and a lower alkyl group having 1 to 6 carbons, or $R_3$ and $R_4$ together comprise a cyclic structure having 4 to 6 carbons;
wherein X is selected from the group hydrogen, a lower alkyl group having between about 1 and 4 carbons, OH, $NH_2$ and a halogen selected from fluorine, chlorine, bromine and iodine;
wherein Z is $(CH_2)_n$;
wherein n equals 1 to 4; and
wherein the sulfamate group is attached at either the 2', 3' or 4' position.

5. The compound of claim 3, wherein $R_1$ and $R_2$ are hydrogen, $R_3$ and $R_4$ are $CH_3$, X is selected from the group hydrogen and Cl, and the sulfamate moiety is attached at the 4'C.

6. The compound of claim 4, wherein $R_1$ and $R_2$ are hydrogen, $R_3$ and $R_4$ are $CH_3$, X is selected from the group hydrogen and Cl, the sulfamate moiety is attached at the 4'C, and n equals 2.

7. A method for treating a patient having an estrogen dependent illness:

a) incorporating into a suitable pharmaceutical carrier one or more compounds having the formula (1):

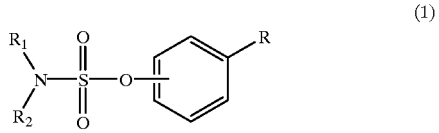
(1)

wherein the aromatic ring together with the R group represent a moiety that blocks an estrogen receptor;

wherein $R_1$ and $R_2$ are independently selected from the group hydrogen and a lower alkyl group having 1 to 6 carbons; and wherein the sulfamate group is attached to the 2'C, 3'C or 4'C of the aromatic ring; and b) administering to said patient an effective amount of the composition of step a).

8. The method of claim 7, wherein said treatment is selected from therapeutic treatment and prophylactic treatment.

9. The method of claim 8, including using as said suitable pharmaceutical carrier physiologic saline, 95 percent dextrose.

10. The method of claim 8, wherein said administration is parenteral.

11. The method of claim 8, wherein said administration is oral.

12. A method for treating a patient having an estrogen dependent illness comprising:

a) incorporating into a suitable pharmaceutical carrier one or more compounds having the formula (1):

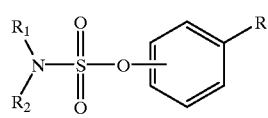

(1)

wherein the aromatic ring together with the R group represent a moiety that blocks an estrogen receptor:

wherein $R_1$ and $R_2$ are independently selected from the group hydrogen and a lower alkyl group having 1 to 6 carbons; and wherein the sulfamate group is attached to the 2'C. 3'C or 4'C of the aromatic ring; and b) administering to said patient an effective amount of the composition of step a); wherein the moiety represented by the aromatic ring together with the R group is selected from the group tamoxifen and tamoxifen derivatives.

13. The method of claim 12, wherein the compound has the formula (2)

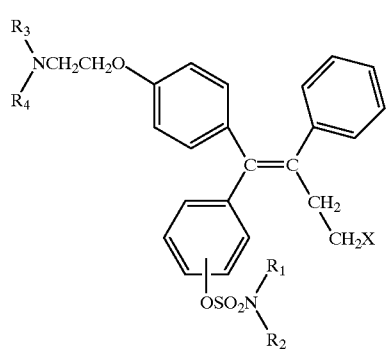

(2)

wherein $R_1$ and $R_2$ are independently selected from the group hydrogen and a lower alkyl group having 1 to 6 carbons;

wherein $R_3$ and $R_4$ are independently selected from the group hydrogen and a lower alkyl group having 1 to 6 carbons, or $R_3$ and $R_4$ together comprise a cyclic structure having 4 to 6 carbons;

wherein X is selected from the group hydrogen, a lower alkyl group having 1 to 4 carbons, OH, $NH_2$ and a halogen selected from fluorine, chlorine, bromine and iodine; and wherein the sulfamate group is attached at either the 2', 3' or 4' position.

14. The method of claim 12, wherein the compound has the formula (3)

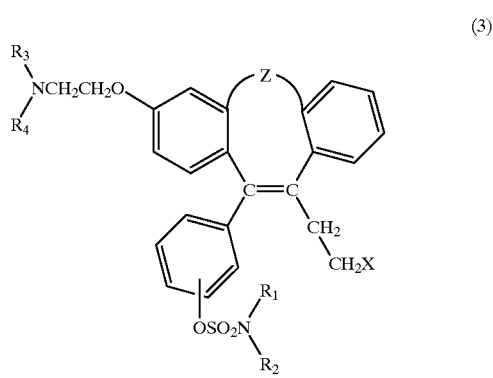

(3)

wherein $R_1$ and $R_2$ are independently selected from the group hydrogen and a lower alkyl group having 1 to 6 carbons;

wherein $R_3$ and $R_4$ are independently selected from the group hydrogen and a lower alkyl group having 1 to 6 carbons, or $R_3$ and $R_4$ together comprise a cyclic structure having 4 to 6 carbons;

wherein X is selected from the group hydrogen, a lower alkyl group having 1 to 4 carbons, OH, $NH_2$ and a halogen selected from fluorine, chlorine, bromine and iodine;

wherein Z is $(CH2)_n$;

wherein n equals 1 to 4; and wherein the sulfamate group is attached at either the 2', 3' or 4' position.

15. The method of claim 14, wherein $R_1$ and $R_2$ are hydrogen, $R_3$ and $R_4$ are $CH_3$, X is selected from the group hydrogen and Cl, and the sulfamate moiety is attached at the 4'C.

16. The method of claim 15, wherein $R_2$ and $R_2$ are hydrogen, $R_3$ and $R_4$ are $CH_3$, X is selected from the group hydrogen and Cl, the sulfamate moiety is attached at the 4'C, and n equals 2.

* * * * *